(12) United States Patent
Radha et al.

(10) Patent No.: US 11,710,573 B2
(45) Date of Patent: Jul. 25, 2023

(54) SELF-LEARNING VERIFICATION METHOD FOR DATA AUTHENTICITY

(71) Applicant: KONINKLIJKE PHILIPS N.V., Eindhoven (NL)

(72) Inventors: Mustafa Ghassan Radha, Eindhoven (NL); Lucas Jacobus Franciscus Geurts, Eindhoven (NL); Mark Anthony Hennessy, Eindhoven (NL); Mark Thomas Johnson, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 342 days.

(21) Appl. No.: 16/870,037

(22) Filed: May 8, 2020

(65) Prior Publication Data

US 2020/0401901 A1    Dec. 24, 2020

Related U.S. Application Data

(60) Provisional application No. 62/864,621, filed on Jun. 21, 2019.

(51) Int. Cl.
| | |
|---|---|
| *G16H 50/70* | (2018.01) |
| *G06N 3/088* | (2023.01) |
| *G16H 10/60* | (2018.01) |
| *G06F 18/22* | (2023.01) |
| *G06F 18/214* | (2023.01) |
| *G06V 40/10* | (2022.01) |

(52) U.S. Cl.
CPC ........... *G16H 50/70* (2018.01); *G06F 18/214* (2023.01); *G06F 18/22* (2023.01); *G06N 3/088* (2013.01); *G16H 10/60* (2018.01); *G06V 40/15* (2022.01)

(58) Field of Classification Search
CPC ...... G06N 3/088; G16H 10/60; G06K 9/6215; G06K 9/6256
See application file for complete search history.

(56) References Cited

U.S. PATENT DOCUMENTS

| | | | |
|---|---|---|---|
| 2013/0041290 A1 | 2/2013 | Albert et al. | |
| 2014/0188770 A1* | 7/2014 | Agrafioti | A61B 5/7267 706/13 |
| 2016/0151022 A1 | 6/2016 | Berlin et al. | |
| 2018/0137939 A1* | 5/2018 | Steiger | G06F 21/44 |

OTHER PUBLICATIONS

Israel, S. et al., "ECG to identify individuals". Pattern Recognition, Jan. 2005.
Kriangsiri, M. et al. "Addressing Security in Medical Sensor Networks". HealthNet, Jun. 11, 2007.

* cited by examiner

Primary Examiner — Mishawn N. Hunter (57) ABSTRACT

A user device that receives plural strings of data corresponding to physiological data, generated from a training model trained in an unsupervised manner using concurrently implemented loss functions, and using a distance metric, relative to a threshold, applied between the plural strings to provide an indication of authenticity.

20 Claims, 5 Drawing Sheets

SELF-LEARNING VERIFICATION METHOD FOR DATA AUTHENTICITY

FIELD OF THE INVENTION

The present invention is generally related to data privacy and authenticity, and more particularly, privacy and authenticity in personal health record services.

BACKGROUND OF THE INVENTION

Today, every new product in the health and wellness industry is equipped with capabilities to generate data. While in many fields this data is already being put to use optimally, for healthcare, it remains a challenge to make use of data generated outside of the hospital. For instance, circumstances may include an outpatient monitoring setting, where a health care professional issues a health monitoring device to a patient for use at home for remote monitoring. Another case may be that the patient already makes use of wearable devices, including smart watches, and may share this data with a health care professional.

There is a reluctance from health care professionals to make use of data generated outside of a health care professional's office or medical/research facility, including the above-described scenarios, as there is little guarantee about the reliability of the data being collected in such a way. For small amounts of data, health care professionals may have the time to inspect the data quality manually to confirm that the data is reliable enough for decision making. However, as the amount of data grows, this may lead to an over-burden on time and/or resources and thus may not be practical and/or economically feasible anymore.

One indicator of data reliability is data authenticity. To be able to make a health decision about a person, one should be assured that the data being analyzed originates from that person. There are potential shortcomings to this approach. For instance, a device may be shared by multiple individuals, or may be handed out to the wrong (e.g., unintended) person. It would be helpful to prevent this type of un-authentic data from creating authenticity issues and any consequential errors resulting from these events.

Also, privacy issues may arise from the communication of data to a central repository, including cloud solutions in health care. For instance, large amounts of sensitive data available in a single place or associated with a single entity online may pose a threat to the privacy of patients, especially when access is given to third parties (e.g., data analysts, insurers, family of the patient, etc.). While simple de-identification methods (e.g., removing personal information) may in part overcome the issue of third party access, there is some concern that communication of (and hence, potentially access to) a sufficient number of physiological signals may potentially form a "fingerprint" of a person.

SUMMARY OF THE INVENTION

One object of the present invention is to ensure authentication of physiological data from a given user. To better address such concerns, in a first aspect of the invention, a device is disclosed that receives plural strings of data corresponding to physiological data, generated from a training model trained in an unsupervised manner using concurrently implemented loss functions, and using a distance metric, relative to a threshold, applied between the plural strings to provide an indication of authenticity. Through this approach, a determination may be made as to whether plural physiological signals were collected from the same person or multiple persons, enabling better authenticity verification of a data stream, which may have various applications in personal health records and outpatient monitoring.

In one embodiment, the learning model comprises a neural network model. At a minimum, the model should be capable of learning patterns from data. Neural networks provide a model that uses backpropagation during a training phase to minimize a loss function, steering the behavior of the learning model to provide an improved solution to data authenticity.

In one embodiment, the loss functions are satisfied by the learning model extracting characteristics of each of the plural sets of user data through the training that maximizes one loss function across users and minimizes another loss function associated with the user. The use of concurrent loss functions introduces adversarial conditioning to the training process, whereby a loss between different people is maximized while a loss within persons is minimized, providing a convergence (e.g., Nash equilibrium) that best satisfies the loss functions.

In one embodiment, the device determines an identifiability metric based on a loss of the learning model. There is no general-purpose way of determining how much a physiological signal collected from an individual may identify that person (e.g., form a fingerprint of the person). Through this approach, accurate decisions about identifiability are enabled when patient data is shared between different parties.

In one embodiment, the learning model is updated for each introduction of an additional source of user data. The model may be continuously trained and improved each time the user adds a new biometric authentication approach that measures some physiological trait. For instance, the addition of a new biometric sensor to the existing one(s) adds another physiological measurement that may be used to strengthen the learning algorithm's ability to minimize entropy of user data and maximize it for other data sources to improve the authenticity of data from a user.

In one embodiment, the learning model is further based on data received responsive to a challenge request, the challenge request prompted by an inability of satisfying the loss functions. For instance, where the physiological data from a given sensor may be insufficient to authenticate the user, a challenge request may be sent to the user, where the user is asked to perform an action that is designed to elicit a physiological response perceivable from the collected data and that will help to identify the user.

These and other aspects of the invention will be apparent from and elucidated with reference to the embodiment(s) described hereinafter.

BRIEF DESCRIPTION OF THE DRAWINGS

Many aspects of the invention can be better understood with reference to the following drawings, which are diagrammatic. The components in the drawings are not necessarily to scale, emphasis instead being placed upon clearly illustrating the principles of the present invention. Moreover, in the drawings, like reference numerals designate corresponding parts throughout the several views.

DETAILED DESCRIPTION OF EMBODIMENTS

Disclosed herein are certain embodiments of a data authentication system and associated methods that learns to extract from any physiological signal a highly subject-specific feature set. In one embodiment, a neural network is trained in an unsupervised fashion to find an identification string by training the algorithm to encode information from the signal into the string that varies as little as possible within-person, but concurrently varies as much as possible across persons. In some embodiments, the data authentication system also performs a privacy preserving function. In one embodiment, the model may be trained multiple times for different types or combinations of physiological signals (e.g., heart rate, respiration, gait, etc.). The obtained loss of the model may be used as a metric of how much the specific sensor type identifies a person, which in turn (the metric) may be used when sharing data with parties that are only allowed to have de-identified data (e.g., for privacy reasons).

Digressing briefly, there is no general-purpose way of determining whether plural physiological signals were collected from the same person or multiple persons. Also, there is no general-purpose way of determining how much a physiological signal collected from an individual may identify that person (e.g., form a fingerprint of the person). Through certain embodiments of a data authentication system, plural strings of data corresponding to plural sets of user physiological data are generated/received, each of the plural strings of data generated based on a learning model, the learning model trained in unsupervised manner using concurrently implemented loss functions that generate each of the plural strings of data in a manner that satisfies the loss functions to provide an indication of authenticity and in some embodiments, an identifiability metric for applications involving privacy preserving measures.

Having summarized certain features of a data authentication system of the present disclosure, reference will now be made in detail to the description of a data authentication system as illustrated in the drawings. While an authentication system will be described in connection with these drawings, there is no intent to limit it to the embodiment or embodiments disclosed herein. For instance, though emphasis is placed on authenticity and/or privacy associated with personal health records that are managed by the user and/or a third party, it should be appreciated by one having ordinary skill in the art that data associated with other data structures, including proprietary or public data structures, are also contemplated to be within the scope of the disclosure. Further, one focus of the description below is on neural networks, and in particular, deep convolutional neural networks, though in some embodiments, pattern recognition using other forms of machine learning (e.g., rules-based approaches, Bayesian/statistical methods, etc.) or other types of neural networks (e.g., recurrent neural networks, spiking neural networks, capsule networks, etc.) are contemplated to be within the scope of the disclosure. Further, although the description identifies or describes specifics of one or more embodiments, such specifics are not necessarily part of every embodiment, nor are all of any various stated advantages necessarily associated with a single embodiment. On the contrary, the intent is to cover all alternatives, modifications and equivalents included within the principles and scope of the disclosure as defined by the appended claims. For instance, two or more embodiments may be interchanged or combined in any combination. Further, it should be appreciated in the context of the present disclosure that the claims are not necessarily limited to the particular embodiments set out in the description.

Figure 1:
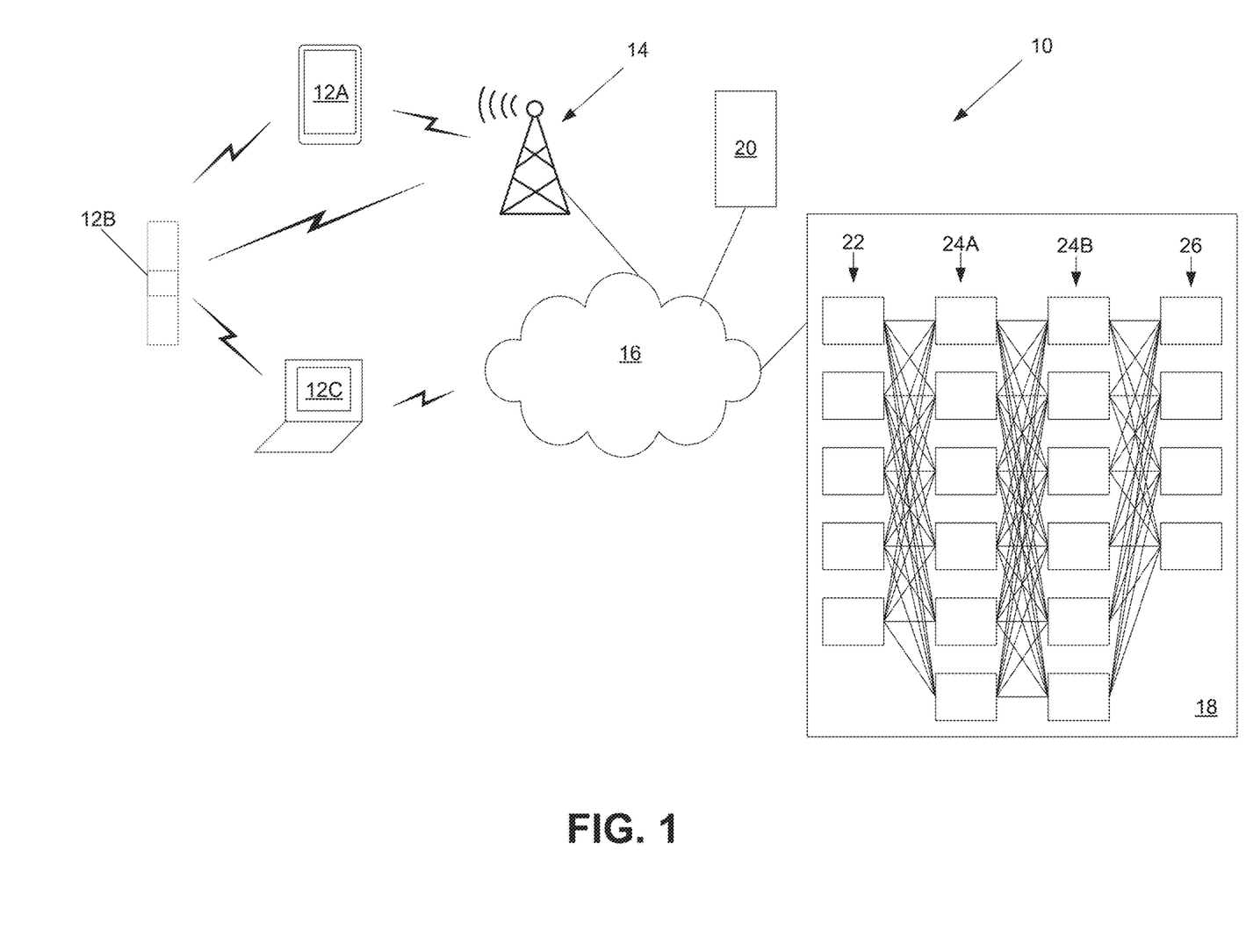
FIG. 1 is a schematic diagram that illustrates an example environment in which a data authentication system is used, in accordance with an embodiment of the invention.

Referring now to FIG. 1, shown is an example environment 10 in which certain embodiments of a data authentication system may be implemented. It should be appreciated by one having ordinary skill in the art in the context of the present disclosure that the environment 10 is one example among many, and that some embodiments of a data authentication system may be used in environments with fewer, greater, and/or different components than those depicted in FIG. 1. The data authentication system may comprise all of the devices depicted in FIG. 1 in one embodiment, or a subset of the depicted devices in some embodiments. The environment 10 comprises a plurality of devices that enable communication of information throughout one or more networks. The depicted environment 10 comprises one or more user devices 12 (e.g., 12A, 12B, and 12C), a wireless/cellular network 14, a network 16, a neural network 18 coupled to the network 16, and the storage device 20. The storage device 20 may include one or more devices for the storage of personal health records. The network 16 may include one or more networks, including a wide area network (WAN), metropolitan area network (MAN), one or more local area networks (LANs), among other networks, and in some embodiments, all or a portion of the networks 14 and 16 may be combined. In some embodiments, the neural network 18 integrated as a part of the network 16. In one embodiment, the neural network 18 comprises plural computational devices or computational nodes (or neurons) in the form of plural logic devices (e.g., multiple-accumulate circuits or MACs), multiple processors (e.g., Tensor Processing Units™, graphics processing units or GPUs, vector processing units or VPUs, field programmable gate arrays or FPGUs, including embedded FPGUs), or multiple computers (e.g., a server network in a cloud computing environment). In some embodiments, the neural network 18 may reside in a single computing device.

The user devices 12 comprise one of a plurality of types of devices, including a smartphone 12A, wearable device or activity tracker 12B, laptop computer 12C, among others (e.g., notebook, notepad, personal digital assistant, pager, Internet of things (IoT) devices (e.g., appliances, automotive devices, etc.)). The user devices 12 may sense and/or collect physiological data and data other than physiological data (e.g., contextual data, including location data, environmental data, etc.). The smartphone 12A may be in communications with the wearable device 12B and/or one or more computing devices of the network 16 and/or neural network 18. The smartphone 12A may include sensing functionality, including such sensor modalities as motion (e.g., acceleration), PPG, and/or ECG sensing. In one embodiment, the smartphone 12A comprises heart and/or breathing rate monitoring using a Philips Vital Signs Camera, or similar functioning devices from other manufacturers, to remotely measure heart and breathing rates using a standard, infrared (IR) based camera by sensing changes in skin color and body movement (e.g., chest movement), among others. ECG measurements may be achieved using electrodes on, for instance, the casing of the smartphone 12A. In some embodiments, the smartphone 12A comprises an accelerometer, gyroscope, and location sensing functionality including a global navigation satellite system (GNSS) receiver, including a global positioning system (GPS) receiver, which tracks and provides location coordinates (e.g., latitude, longitude, altitude) for the device 12A. The smartphone 12A may further include one or more interfaces for providing feedback of a monitored condition and/or activity, including a display screen (e.g., touch-type) to provide health data monitored or accessed by the smartphone 12A. The smartphone 12A comprises wireless/cellular communication functionality, including cellular, streaming and/or broadband (e.g., 3G, 4G, 5G, LoRa, etc.), Wi-Fi, Blue-tooth, NFC, etc., which may be used for the communication of sensing data (e.g., health data) and/or feedback information among the devices 12 and/or the neural network 18.

The wearable device 12B is typically worn by the user (e.g., around the wrist or torso, as a patch, or attached to an article of clothing, or even embedded within a user), and comprises a plurality of sensors that track motion and/or physical activity of the user (e.g., steps, swim strokes, pedaling strokes, limb movement, etc.), activity type (walking, cycling, running, etc.) and is further configured to sense/measure or derive physiological parameters (e.g., heart rate, average heart rate, resting heart rate, inter-beat intervals, blood pressure, pulse rate, respiration, skin temperature, etc.) based on the sensor data, and optionally sense various other parameters (e.g., context, including outdoor temperature, humidity, location, etc.) pertaining to the surrounding environment of the wearable device 12B. In one embodiment, the wearable device 12B comprises an electrocardiographic (ECG) sensor and a photoplethysmographic (PPG) sensor and an accelerometer and/or gyroscope. In some embodiments, the wearable device 12B may comprise a GNSS receiver, including a global positioning system (GPS) receiver, which tracks and provides location coordinates (e.g., latitude, longitude, altitude) for the device 12B.

Data collected by the one or more sensors of the wearable device 12B may be communicated to the user via an interface (e.g., an integrated display) on the wearable device 12B. In one embodiment, the wearable device 12B uses the integrated display to also provide feedback to the user of a monitored condition and/or activity (e.g., health data). Such data collected by the wearable device 12B may be communicated to the smartphone 12A, the laptop 12C, and/or to other devices coupled to the neural network 18, as well as (or alternatively) communicated to the storage device 20. Communication functionality of the wearable device 12B includes wireless functionality (e.g., near field communications (NFC), Blue-tooth, 802.11-based technology, streaming technology, including LoRa, and/or broadband technology including 3G, 4G, 5G, etc.) and/or wired functionality (e.g., via universal serial bus (USB), etc.).

The laptop 12C comprises typical data processing functionality, and communication functionality includes wireless communications (e.g., NFC, Blue-tooth, 802.11-based technology, streaming technology, including LoRa, and/or broadband technology including 3G, 4G, 5G, etc.) and wired functionality (e.g., USB, Ethernet, etc.) to receive (e.g., from the neural network 18, the device 12B, and/or the storage device 20) health data.

One or more of the user devices 12 may include middleware (e.g., web services interfaces or web application programming interfaces (APIs) (e.g., SOAP, HTTP, XML, etc.), other APIs, etc.) that enable communications with remote computing devices (e.g., to access electronic health records and/or other health data of the storage device 20 and/or for communications with the neural network 18). For instance, cooperation between the user devices 12 and devices of the neural network 18 may be facilitated (or enabled) through the use of one or more APIs that may define one or more parameters that are passed between a calling application and other software code such as an operating system, library routine, function that provides a service, that provides data, or that performs an operation or a computation. The API may be implemented as one or more calls in program code that send or receive one or more parameters through a parameter list or other structure based on a call convention defined in an API specification document. A parameter may be a constant, a key, a data structure, an object, an object class, a variable, a data type, a pointer, an array, a list, or another call. API calls and parameters may be implemented in any programming language. The programming language may define the vocabulary and calling convention that a programmer employs to access functions supporting the API. In some implementations, an API call may report to an application the capabilities of a device running the application, including input capability, output capability, processing capability, power capability, and communications capability.

In one embodiment, the storage device 20 may comprise a secure personal health records storage that is managed by the user and/or a third party personal health records provider (or other types of providers, such as activity monitor providers). In one embodiment, physiological data stored in the storage device 20 comprises de-identified data that, when shared with authorized users, maintains the data anonymously.

When the storage device 20 (and/or the neural network 18) is part of a cloud service or services, the storage device(s) 20 and/or the devices of the neural network 18 may comprise an internal cloud, an external cloud, a private cloud, or a public cloud (e.g., commercial cloud). For instance, a private cloud may be implemented using a variety of cloud systems including, for example, Eucalyptus Systems, VMWare vSphere®, or Microsoft® HyperV. A public cloud may include, for example, Amazon EC2®, Amazon Web Services®, Terremark®, Savvis®, or GoGrid®. Cloud-computing resources provided by these clouds may include, for example, storage resources (e.g., Storage Area Network (SAN), Network File System (NFS), and Amazon S3®), network resources (e.g., firewall, load-balancer, and proxy server), internal private resources, external private resources, secure public resources, infrastructure-as-a-services (IaaSs), platform-as-a-services (PaaSs), or software-as-a-services (SaaSs). The cloud architecture may be embodied according to one of a plurality of different configurations. For instance, if configured according to MICROSOFT AZURE™, roles are provided, which are discrete scalable components built with managed code. Worker roles are for generalized development, and may perform background processing for a web role. Web roles provide a web server and listen for and respond to web requests via an HTTP (hypertext transfer protocol) or HTTPS (HTTP secure) endpoint. VM roles are instantiated according to tenant defined configurations (e.g., resources, guest operating system). Operating system and VM updates are managed by the cloud. A web role and a worker role run in a VM role, which is a virtual machine under the control of the tenant. Storage and SQL services are available to be used by the roles. As with other clouds, the hardware and software environment or platform, including scaling, load balancing, etc., are handled by the cloud.

In some embodiments, the storage device(s) 20 and/or the devices of the neural network 18 may be configured into multiple, logically-grouped servers (run on server devices), referred to as a server farm. The devices may be geographically dispersed, administered as a single entity, or distributed among a plurality of server farms, executing one or more applications on behalf of, or processing data from, one or more of the user devices 12. The devices within each farm may be heterogeneous. One or more of the devices may operate according to one type of operating system platform (e.g., WINDOWS NT, manufactured by Microsoft Corp. of Redmond, Wash.), while one or more of the other devices may operate according to another type of operating system platform (e.g., Unix or Linux). The devices may be logically grouped as a farm that may be interconnected using a wide-area network (WAN) connection or medium-area network (MAN) connection.

The wireless/cellular network 14 may include the necessary infrastructure to enable wireless and/or cellular communications between the user devices 12 and one or more other devices (e.g., devices of the network 16, devices of the neural network 18, the storage device 20). There are a number of different digital cellular technologies suitable for use in the wireless/cellular network 14, including: 3G, 4G, 5G, GSM, GPRS, CDMAOne, CDMA2000, Evolution-Data Optimized (EV-DO), EDGE, Universal Mobile Telecommunications System (UMTS), Digital Enhanced Cordless Telecommunications (DECT), Digital AMPS (IS-136/TDMA), and Integrated Digital Enhanced Network (iDEN), among others, as well as Wireless-Fidelity (Wi-Fi), 802.11, streaming, for some example wireless technologies.

The neural network 18 is depicted as a deep (convolutional) neural network comprising an input layer 22, plural hidden layers 24 (e.g., 24A, 24B), and an output layer 26. The number of computational nodes depends on the application, and the quantity of nodes and/or layers depicted in FIG. 1 is merely for illustrative purposes. The neural network 18 is configured to train one or more learning models and implement those learning models according to an inference engine. In some embodiments, the training and implementation of the learning models may be achieved in different devices or sets of devices. In some embodiments, training and implementation as an inference engine are achieved in a single device or single set of devices.

Figure 2:
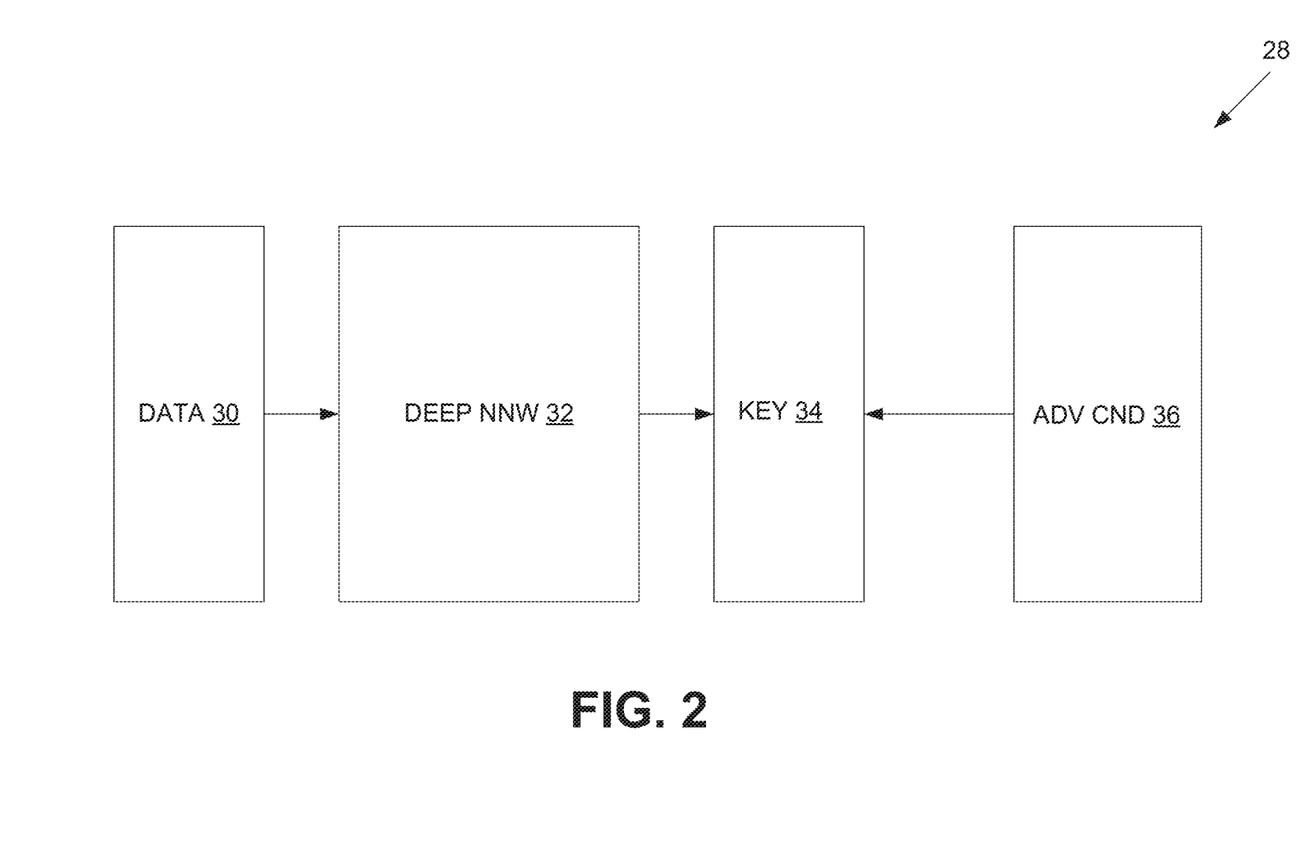
FIG. 2 is a block diagram that conceptually illustrates a data authentication system, in accordance with an embodiment of the invention.

Attention is now directed to FIG. 2, which conceptually illustrates an example data authentication system 28. In one embodiment, the data authentication system 28 comprises one or more data sets (DATA) 30 that are received by a deep convolutional/temporal architecture (DEEP NNW) 32 (e.g., neural network, such as neural network 18, FIG. 1). The deep convolutional/temporal architecture 32 generates an identification string or key (KEY) 34. The generation of the identification string 34 may be performed in conjunction with adversarial conditioning (ADV CND) 36, as explained further below. In particular, the data authentication system 28 learns to extract from any physiological signal a highly subject-specific feature set. This is done by training the neural network 32 in an unsupervised fashion to find the identification string 34. For instance, training includes training an algorithm/learning model to encode information from the data set 30 (e.g., physiological data) from the signal into the string 34 that varies as little as possible within-person (decreased entropy), but simultaneously varies as much as possible across persons (increased entropy). That is, loss functions are used to maximize the entropy across sources and minimize it within sources. Adversarial conditioning 36 (e.g., using reverse gradient descent) may be included to make the feature set invariant to certain conditions such as disease, medication or seasonal effects on the physiological signal (which may otherwise lead to incorrectly classifying data collected during these deviant conditions as un-authentic). The algorithm or learning model is trained on one or more sensors modalities collected from a large set of persons (e.g., in a personal health cloud platform). The loss after training is inversely proportional to the quality of the identification string. A lower loss corresponds to a more unique string that can be generated from the data sequence.

Describing the training process or phase further, the computational nodes (neural layers and cells) of the deep convolutional neural network 32 receives the data set(s) as input and initially generates a string of features according to the initial random behavior of the nodes. The network 32 applies a loss function (e.g., gradient descent) on the string of features and through an iterative process propagates (e.g., using backpropagation) each result (of application of the loss function) back to a learning model to steer the learning model behavior in such a manner that improves the loss. After several iterations, the model's computational nodes learn to generate string features that have a better loss function, a process also referred to as minimizing the loss function. Eventually, the model's loss function stops improving, or rather, the model converges, where there exists no additional changes that the model can make to its architecture to have a better loss. Accordingly, the learning model exhibits a final loss, and if the loss is very low, the model works well, and if it is very high, more needs to be done (as explained below). With the application of adversarial conditioning 36, the learning model has two loss functions that are effectively in conflict with each other, with one loss function maximizing the loss between different people and another loss function minimizing the loss within people. The training is implemented with the loss functions implemented concurrently (simultaneously), resulting in a Minimax game that steers the learning model to generate a feature vector that satisfies both loss functions as well as possible, with convergence corresponding to, for instance, a Nash Equilibrium in the context of Minimax games.

As indicated above, the data authentication system 28 enables better authenticity verification of a data stream. The learning model can be used to generate a string/key from a physiological signal (on which it was trained), where the algorithm/learning model determines through the training process explained above which characteristics to extract from the data set(s) 30 that meet the criterion of being highly similar within-subject, and highly dissimilar across subjects. For example, if the learning model is trained on heart rate data, the learning model may be used to extract an identifying key from the heart rate data. During execution of an inference engine that uses the trained learning models, the key may be compared to a previous measurement of the same person. Using a distance metric (e.g., Euclidean distance, though other distance metrics may be used, including Mahalanobis distance), a lower Euclidean distance between the previous and current key means the likelihood is high that the data originates from the same person. A high distance warrants the possibility of un-authentic data (e.g. device is worn by someone else). The learning model may be trained on existing data, and used on future data, but it may also be run on the same data set to detect unauthentic recordings in historical acquisitions. Note that the determination of high and low may be relative to a threshold. The threshold may be learned based on historical data from the user and/or population data. In some embodiments, the threshold may be fixed (e.g., programmed based on the type of physiological signal). Note that in some embodiments, a learning model is trained on a given data modality, which can be re-used by the inference engine (e.g., for the same sensor(s)) for new data. In some embodiments, the learning model is trained with each iteration of new data, which is respectively used by the inference engine for each new data.

An example of data authentication based on the learning model is described below in conjunction with a distance metric depicted in FIG. 3, with the understanding that this example is merely illustrative of some of the principles described above. Assume an outpatient monitoring solution, where a patient is at home using a health watch for a few weeks. For every new day, d, of data, the network computes a key or identification string $K_d$. For one user, the Euclidian distance is between $K_d$ and $K_{d-1}$, $K_{d-2}$, ..., $K_{d-n}$, where n is a configurable parameter denoting the amount of days of history to consider. Thus, the distance is computed as follows:

$$dist = \frac{1}{n} \sum_{i=d-n}^{d-1} EUCLID(K_d, K_i) \qquad (Eq. 1)$$

While $K_d$ in practice is likely to be comprised of a long vector of numbers, for this example, the vector is simplified to a single number between 0 and 10. Again, in practice, a single number is not sufficient, but this provides an example illustrative of a Euclidian distance in 1-dimensional space that is simply the difference in values. Now, assume one of the users, after a week of monitoring, is asked by a friend to try out the wearable, so the user lends it to the friend. Referring now to FIG. 3, shown is a graph diagram 38 with the computed key 40 for each change in distance 42. That is, FIG. 3 illustrates how the key or string, $K_d$ changes from a value around 3-4 to a much higher value. As shown, the distance 42 immediately increases on that day (e.g., day 8, with a value of 5) and then stabilizes back. This peak in the distance may be used to raise an alarm regarding data authenticity. In one embodiment, a threshold is used to indicate whether this value is abnormally high. If so, then exceeding the threshold triggers a warning in the system that the source of the data might have changed on that day.

Note that the learning model may be trained multiple times for different types of physiological data/signals (e.g. heart rate, respiration, gait, etc.). Also, one or more additional sensor modalities may be added to improve the loss function (e.g., if the loss is unacceptable).

As explained above, in some embodiments of a data authentication system, privacy preservation may also be achieved, such as through identifiability metric generation. That is, the obtained loss of the learning model may be used as a metric of how much the specific sensor type identifies a person. Whereas a lower loss is sought for the data authentication features, for the use case of de-identification (e.g., for privacy), a bad loss function is desired, since then there is confidence that if this de-identified user data is shared with a third party, the third party is not likely to be able to back trace from which person that data originated. The identifiability metrics may be used when sharing data with parties that are only allowed to have de-identified data (for privacy reasons). An improved model may be obtained by training the model simultaneously using a multitude of signals. For instance, assume that signals corresponding to [heart rate+respiration rate] have a loss of 2.0, and signals corresponding to [heart rate+gait] have a loss of 0.4. The implication is that it is a larger security concern to share the [heart rate+gait] combination as it is more likely that the person's data may form a fingerprint of that person.

In some embodiments, certain techniques may be used to strengthen the authentication and/or identification. For instance, each new sensor added to by the user provides an extra factor in the authentication/identifiability metric and can strengthen authentication by providing extra physiological inputs on a more continuous basis, and may improve the possibility of generating a unique key to identify the user of a device. The learning model may be continuously trained and improved each time the user adds a new biometric authentication approach that measures some physiological trait. The addition of a new biometric sensor to the existing ones adds another physiological measurement that may be used to strengthen the ability of the learning algorithm(s) to minimize entropy of user data and maximize it for other data sources to improve the authenticity of data from a user. Note that these strengthening measures may also be used as a failover method in generating a key (e.g., if there is an unacceptable quantity of errors in detection of the user). In one embodiment, the key is only generated to identify users, whereas for privacy implementations, it is sufficient to train the learning model and evaluate the final loss (without key generation).

In some embodiments, recording the provenance of each identification key generated (e.g., which may be a combination of digital signatures from each biometric sensor) for a user may be implemented as each physiological measurement sensor added is likely to contribute to entropy minimization of the generated key for the user. If the user removes a biometric sensor, then the user should be identifiable from previous keys generated with the remaining sensors.

In some embodiments, a regular biometric challenge response may be used as a way to strengthen the authenticity of data from a user. Issuing a biometric challenge/response at times of significant or heightened exertion may be used to maintain the session during which a data stream is being generated to strengthen the authenticity and provenance of the data from a user. For instance, assume a key is generated based on user ECG data, and the loss is unacceptable on this data alone (e.g., no improvement in the loss function and not sufficient to identify the user, such as according to a score or scale). The data authentication system may issue a challenge request to perform an action (e.g., activity, like perform ten burpees). The challenge is directed at eliciting a physiological response that is perceivable from the collected data corresponding to a monitorable action or activity (e.g., triggers a change in the ECG data). The physiological response may further identify the user given the variation in responses to such an activity among different individuals.

Figure 4:
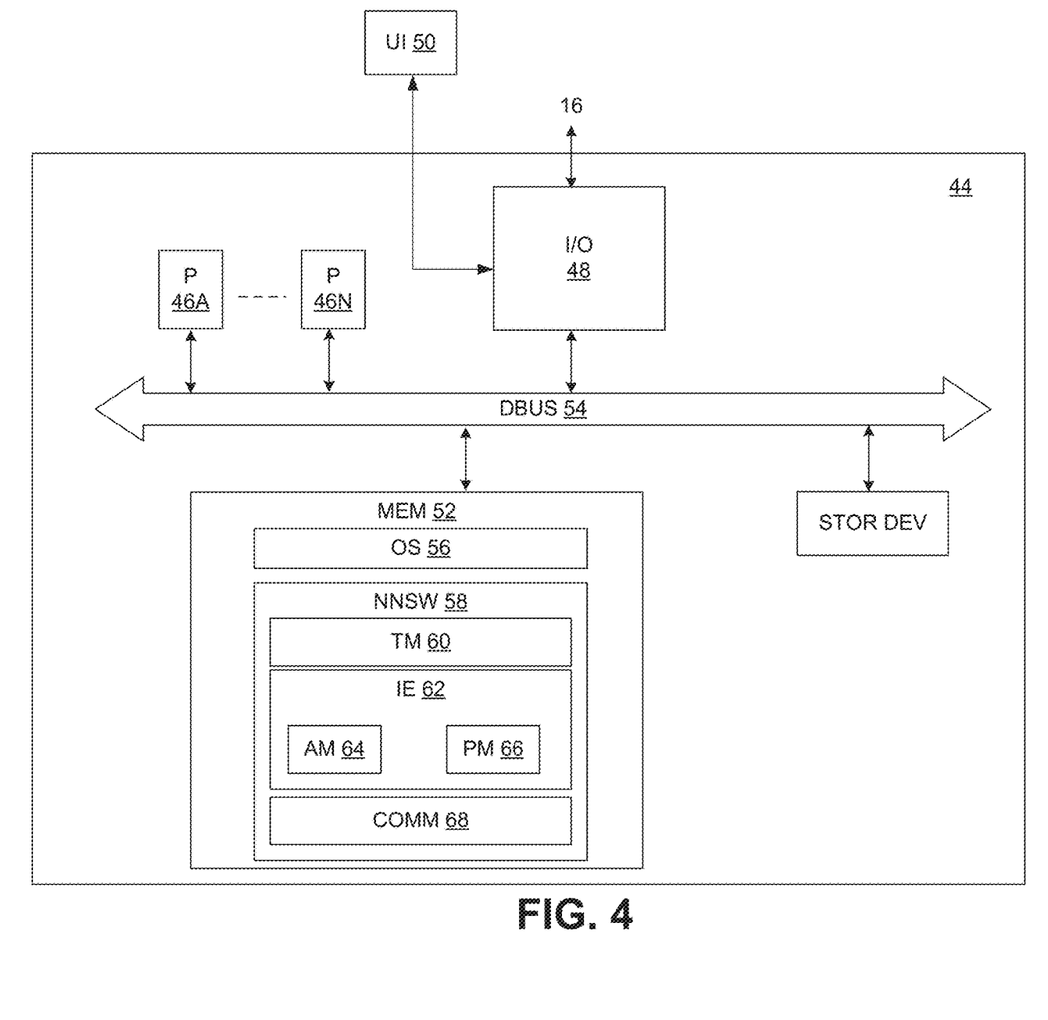
FIG. 4 is a block diagram that illustrates an example device running data authentication software, in accordance with an embodiment of the invention.

Having described certain embodiments of a data authentication system, attention is directed to FIG. 4, which illustrates an embodiment of an example computing device 44 that may be used to implement an embodiment of a data authentication system. The software and hardware architecture of the computing device 44 may be used to implement a neural network in certain embodiments, though as indicated above, certain embodiments may use multiple computing devices in the form of multiple computers or servers (e.g., in cloud or server farm configuration), multiple processors, and/or multiple logic units (e.g., application integrated circuits). That is, nodes of a neural network may be embodied as multiple cores or processors residing within the computing device 44, or in some embodiments, the computing device 44 may represent one (or more) computational nodes among a plurality of nodes (e.g., computing devices) in some embodiments that operate in, say, peer-to-peer fashion. One having ordinary skill in the art should appreciate in the context of the present disclosure that the example computing device 44 is merely illustrative of one embodiment, and that some embodiments of computing devices may comprise fewer or additional components, and/or some of the functionality associated with the various components depicted in FIG. 4 may be combined, or further distributed among additional modules or computing devices, in some embodiments. It should be appreciated that certain well-known components of computer systems are omitted here to avoid obfuscating relevant features of the computing device 44.

In one embodiment, the computing device 44 comprises one or more processors (P) 46 (e.g., 46A . . . 46N), input/output (I/O) interface(s) 48 (I/O), one or more user interfaces (UI) 50, which may include one or more of a keyboard, mouse, microphone, speaker, etc.), and memory 52 (MEM), all coupled to one or more data busses, such as data bus 54 (DBUS). In some embodiments, the user interfaces may be coupled directly to the data bus 54. The memory 52 may include any one or a combination of volatile memory elements (e.g., random-access memory RAM, such as DRAM, and SRAM, etc.) and nonvolatile memory elements (e.g., ROM, Flash, solid state, EPROM, EEPROM, hard drive, tape, CDROM, etc.). The memory 52 may store a native operating system, one or more native applications, emulation systems, or emulated applications for any of a variety of operating systems and/or emulated hardware platforms, emulated operating systems, etc. In some embodiments, a separate storage device (STOR DEV) may be coupled to the data bus 54 or as a network-connected device (or devices) via the I/O interfaces 48 and the network 16 (FIG. 1). The storage device may be embodied as persistent memory (e.g., optical, magnetic, and/or semiconductor memory and associated drives), and in some embodiments, may be used to store data depicted as stored in storage device 20 (FIG. 1). In some embodiments, the storage device or memory 52 may store the physiological (and non-physiological) data of the user (or users).

In the embodiment depicted in FIG. 4, the memory 52 comprises an operating system 56 (OS), and neural network software (NNSW) 58, which includes a training module (TM) 60 and an inference engine (IE) 62 that comprises an authentication module (AM) 64 and a privacy module (PM) 66. The neural network software 58 further comprises a communications module (COMM) 68. Note that the memory 52 may also be referred to herein as a non-transitory, computer readable storage medium.

Figure 3:
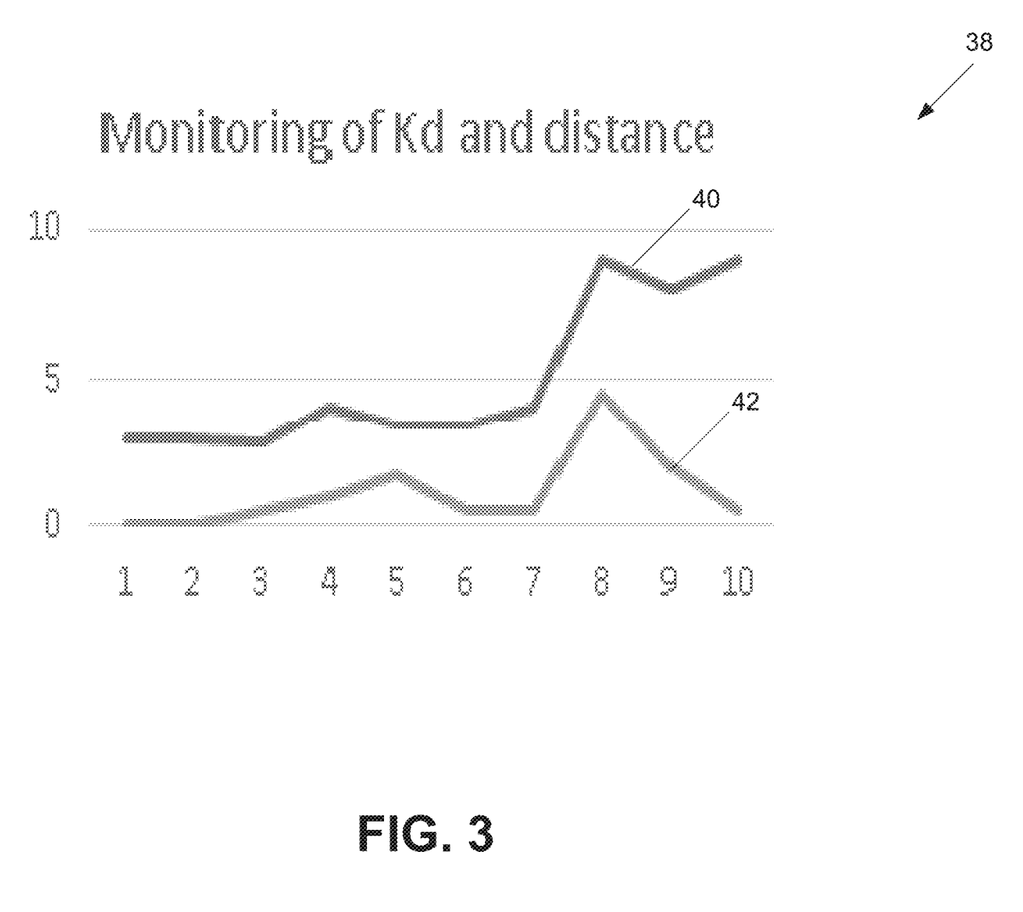
FIG. 3 is a graph diagram that conceptually illustrates application of a distance metric, in accordance with an embodiment of the invention.

The neural network software 58 comprises instructions (e.g., executable code) that perform at least the functions described in association with the data authentication system 28 of FIGS. 2-3. The neural network software 58 may comprise a deep convolutional/temporal neural network or other types of neural networks or pattern recognition methodologies, as described above. The training module 60 (which includes instructions or executable code) trains a learning model or learning models based on unsupervised training and the use of plural loss functions that are maximized and minimized according to adversarial conditioning techniques. The learning model(s) are trained on physiological data sets and/or modalities for one or more users, and may include different models for different types of physiological data (e.g., heart rate, respiration rate, gait, etc.) and/or for one or more sensor modalities. The learning model(s) are used to generate strings of data or keys that are used by the inference engine 62 (which includes instructions or executable code) to authenticate the user data or determine an identifiability metric for privacy functions. In one embodiment, the authentication module 64 performs the functions of applying one of a plurality of types of distance metrics to different strings generated by the learning model from temporally different sets of user data and comparing to a dynamic or predefined threshold to provide an indication of authenticity. The indicator may be communicated, using the communication software 68, to one of the user devices 12 (FIG. 1) or other devices (e.g., devices of, or connected to, the network 16), or the indicator may be a triggering signal communicated to another device to present the indication of authenticity. The presented indicator may be a visible presentation (e.g., symbols and/or alphanumerics that present an alert when there the likelihood of inauthenticity, a probability or corresponding confidence index of authenticity, and/or other mechanisms for conveying the authenticity to the user or caregiver), an audible alert, and/or a tactile alert. In one embodiment, the privacy module 66 performs the functions of generating an identifiability metric based on a loss of the loss functions for different combinations of physiological signals that represents a risk of sharing the data with a third party. Note that, though physiological data has been the focus herein, non-physiological data may be the subject of evaluation as well or alternatively. For instance, social media data is one example of a use case, where the data is sometimes sold to advertisers, and for which anonymizing the data and determining the risk from such sharing of anonymized data is important. The communication of the identifiability metric and/or manner of presentation of the identifiability metric is similar to that of the indicator of authenticity, where alerts may be presented as symbols and/or alphanumerics (e.g., symbols, such as red flags for recommending no sharing, yellow flags for representing caution, and green flags for recommending sharing with confidence, likelihood of risk in terms of probabilities or a corresponding risk index, etc.), audible, and/or tactile methods of presentation. In some embodiments, the output of the privacy module 66 may merely be to disallow any sharing of the user data (with or without feedback of the determination to the user or caregiver) from the storage device 20 or other storage component or system. The neural network software 58 is further configured to implement the aforementioned techniques to improve the loss functions, including the prompting of a challenge request, the updating of the learning model(s) based on added (or removed) sensor modalities (e.g., accelerometers, optical sensors, etc.).

The communications module 68 is configured to communicate the indicators of authenticity and/or privacy (e.g., indication of privacy risk), in cooperation with server, cable modem, telephony, and/or wireless hardware using the corresponding communication protocols, to other devices. In some embodiments, the communications module 68 may work in conjunction with a web server module of the neural network software 58 to present the indicators on a web page.

Note that functionality for the various software modules described above may be distributed and/or duplicated among a plurality of computing devices, combined into fewer modules, or distributed among additional modules. In some embodiments, functionality of one or more of the software modules may instead be performed in hardware.

Execution of the neural network software 58 and software modules 60-68 may be implemented by the one or more processors 46 under the management and/or control of the operating system 56. The processor(s) 46 may be embodied as a custom-made or commercially available processor (e.g., TPUs, GPUs, VPUs), a central processing unit (CPU) or an auxiliary processor among several processors, a semiconductor based microprocessor (in the form of a microchip), a macroprocessor, one or more application specific integrated circuits (ASICs), field programmable gate arrays (FPGUs), a plurality of suitably configured digital logic gates, and/or other well-known electrical configurations comprising discrete elements both individually and in various combinations to coordinate the overall operation of the computing device 44.

The I/O interfaces 48 comprise hardware and/or software to provide one or more interfaces to devices coupled to the network 16 (FIG. 1) and/or wireless/cellular network 14 (FIG. 1), as well as to other devices such as the user interface 50. In other words, the I/O interfaces 48 may comprise any number of interfaces for the input and output of signals (e.g., analog or digital data) for conveyance of information (e.g., data) over various networks and according to various protocols and/or standards. The user interfaces 50 may include a keyboard, mouse, microphone, immersive head set, etc., which enable input and/or output by an administrator or other user.

When certain embodiments of the computing device 44 are implemented at least in part with software (including firmware), it should be noted that the software (e.g., the neural network software 58 and associated modules 60-68) can be stored on a variety of non-transitory computer-readable (storage) medium for use by, or in connection with, a variety of computer-related systems or methods. In the context of this document, a computer-readable medium may comprise an electronic, magnetic, optical, or other physical device or apparatus that may contain or store a computer program (e.g., executable code or instructions) for use by or in connection with a computer-related system or method. The software may be embedded in a variety of computer-readable mediums for use by, or in connection with, an instruction execution system, apparatus, or device, such as a computer-based system, processor-containing system, or other system that can fetch the instructions from the instruction execution system, apparatus, or device and execute the instructions.

When certain embodiments of the computing device 44 are implemented at least in part with hardware, such functionality may be implemented with any or a combination of the following technologies, which are all well-known in the art: a discrete logic circuit(s) having logic gates for implementing logic functions upon data signals, an application specific integrated circuit (ASIC) having appropriate combinational logic gates, a programmable gate array(s) (PGA), a field programmable gate array (FPGA), TPUs, GPUs, and/or other accelerators/co-processors, etc.

Figure 5:
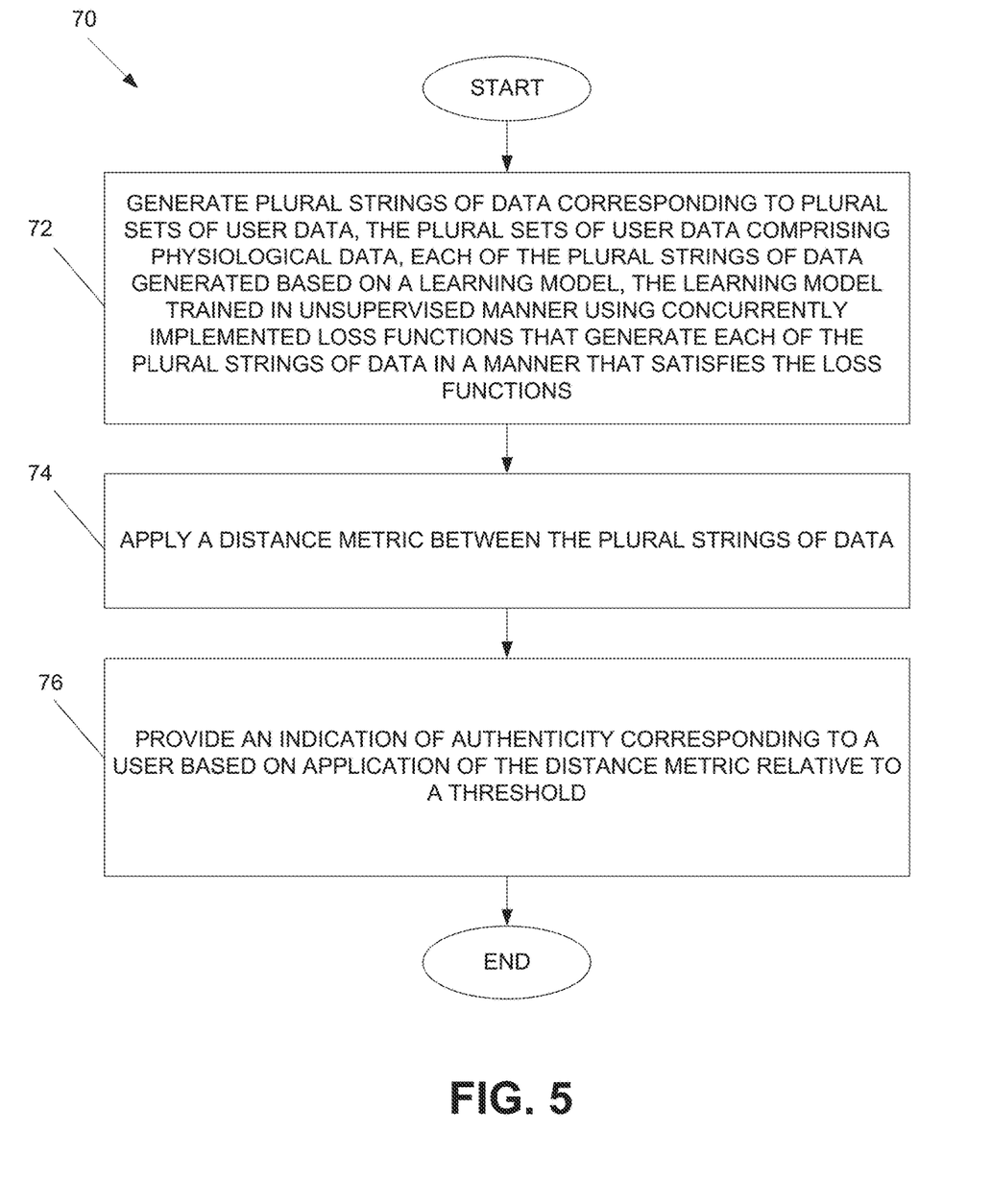
FIG. 5 is a flow diagram that illustrates an example data authentication method, in accordance with an embodiment of the invention.

Having described certain embodiments of a data authentication system, it should be appreciated that one embodiment of an example data authentication method, depicted in FIG. 5 and denoted as method 70, which is shown bounded by a start and end, comprises generating plural strings of data corresponding to plural sets of user data, the plural sets of user data comprising physiological data, each of the plural strings of data generated based on a learning model, the learning model trained in unsupervised manner using concurrently implemented loss functions that generate each of the plural strings of data in a manner that satisfies the loss functions (72); applying a distance metric between the plural strings of data (74); and providing an indication of authenticity corresponding to a user based on application of the distance metric relative to a threshold (76).

Any process descriptions or blocks in flow diagrams should be understood as representing modules, segments, or portions of code which include one or more executable instructions for implementing specific logical functions or steps in the process, and alternate implementations are included within the scope of the embodiments in which functions may be executed out of order from that shown or discussed, including substantially concurrently or in reverse order, depending on the functionality involved, as would be understood by those reasonably skilled in the art of the present disclosure. In some embodiments, one or more steps may be omitted, or further steps may be added.

In one embodiment, a device is disclosed, comprising: a memory comprising instructions; and one or more processors configured by the instructions to: receive plural strings of data corresponding to plural sets of user data, the plural sets of user data comprising physiological data, each of the plural strings of data generated based on a learning model, the learning model trained in unsupervised manner using concurrently implemented loss functions that generate each of the plural strings of data in a manner that satisfies the loss functions; apply a distance metric between the plural strings of data; and provide an indication of authenticity corresponding to a user based on application of the distance metric relative to a threshold.

In one embodiment, the preceding device, wherein the one or more processors are configured by the instructions to indicate that at least one of the plural strings of data lacks authenticity as being sourced from a source other than the user when the distance metric is higher than a threshold.

In one embodiment, any one of the preceding devices, wherein the learning model comprises a neural network model.

In one embodiment, any one of the preceding devices, wherein the plural sets of user data further comprise data other than physiological data.

In one embodiment, any one of the preceding devices, wherein the loss functions are satisfied by the learning model extracting characteristics of each of the plural sets of user data through the training that maximizes one loss function across users and minimizes another loss function associated with the user.

In one embodiment, any one of the preceding devices, wherein the learning model is trained multiple times for different types of physiological data.

In one embodiment, any one of the preceding devices, wherein a loss of the learning model from the training is based on the learning model trained simultaneously using data sets from two or more different types of physiological data.

In one embodiment, any one of the preceding devices, wherein the one or more processors are further configured by the instructions to determine an identifiability metric based on a loss of the learning model.

In one embodiment, any one of the preceding devices, wherein the one or more processors are further configured by the instructions to provide an indication of privacy risk before sharing of the user data based on the identifiability metric.

In one embodiment, any one of the preceding devices, wherein the learning model is updated for each introduction of an additional source of user data.

In one embodiment, any one of the preceding devices, wherein the learning model is further based on data received responsive to a challenge request, the challenge request prompted by an inability of satisfying the loss functions.

In one embodiment, any one of the preceding devices, wherein the challenge request comprises a request for the user to perform an action, wherein the data that is received responsive to the challenge request corresponds to a physiological response that is perceivable and used to identify the user.

In one embodiment, a method is disclosed, the method implemented by any one of the preceding devices.

In one embodiment, disclosed is a non-transitory, computer readable storage medium comprising instructions that executes the preceding method.

In one embodiment, a method is disclosed, the method implemented by one or more computational nodes of a neural network, the method comprising: generating plural strings of data corresponding to plural sets of user data, the plural sets of user data comprising physiological data, each of the plural strings of data generated based on a learning model, the learning model trained in unsupervised manner using concurrently implemented loss functions that generate each of the plural strings of data in a manner that satisfies the loss functions; applying a distance metric between the plural strings of data; and providing an indication of authenticity corresponding to a user based on application of the distance metric relative to a threshold.

In one embodiment, the preceding method, further comprising training the learning model.

In one embodiment, any one of the preceding methods, wherein the training further comprises using adversarial conditioning during implementation of the loss functions.

In one embodiment, any one of the preceding methods, further comprising determining an identifiability metric based on a loss of the learning model.

In one embodiment, any one of the preceding methods, further comprising providing an indication of privacy risk before sharing of the user data based on the identifiability metric.

In one embodiment, any one of the preceding methods, further comprising updating the learning model for each introduction of an additional source of user data.

In one embodiment, any one of the preceding methods, further comprising presenting a challenge request to the user to engage in a monitorable action, the challenge request prompted by an inability of satisfying the loss functions.

In one embodiment, a non-transitory, computer readable storage medium is disclosed, the non-transitory, computer readable storage medium comprising instructions that, when executed by one or more processors, causes the one or more processors to: receive plural strings of data corresponding to plural sets of user data, the plural sets of user data comprising physiological data, each of the plural strings of data generated based on a learning model, the learning model trained in unsupervised manner using concurrently implemented loss functions that generate each of the plural strings of data in a manner that satisfies the loss functions; apply a distance metric between the plural strings of data; and provide an indication of authenticity corresponding to a user based on application of the distance metric relative to a threshold.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims. Note that various combinations of the disclosed embodiments may be used, and hence reference to an embodiment or one embodiment is not meant to exclude features from that embodiment from use with features from other embodiments. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage. A computer program may be stored/distributed on a suitable medium, such as an optical medium or solid-state medium supplied together with or as part of other hardware, but may also be distributed in other forms. Any reference signs in the claims should be not construed as limiting the scope.

The invention claimed is:

1. A device, comprising:
a memory comprising instructions; and
one or more processors configured by the instructions to:
receive plural strings of data corresponding to plural sets of user data, the plural sets of user data comprising physiological data, each of the plural strings of data generated based on a learning model, the learning model trained in unsupervised manner using concurrently implemented loss functions that generate each of the plural strings of data in a manner that satisfies the loss functions;
apply a distance metric between the plural strings of data;
provide an indication of authenticity corresponding to a user based on application of the distance metric relative to a threshold; and
indicate that at least one of the plural strings of data lacks authenticity as being sourced from a source other than the user when the distance metric is higher than a threshold.

2. The device of claim 1, wherein the learning model comprises a neural network model.

3. The device of claim 1, wherein the plural sets of user data further comprise data other than physiological data.

4. The device of claim 1, wherein the loss functions are satisfied by the learning model extracting characteristics of each of the plural sets of user data through the training that maximizes one loss function across users and minimizes another loss function associated with the user.

5. The device of claim 1, wherein the learning model is trained multiple times for different types of physiological data.

6. The device of claim 1, wherein a loss of the learning model from the training is based on the learning model trained simultaneously using data sets from two or more different types of physiological data.

7. The device of claim 1, wherein the one or more processors are further configured by the instructions to determine an identifiability metric based on a loss of the learning model.

8. The device of claim 7, wherein the one or more processors are further configured by the instructions to provide an indication of privacy risk before sharing of the user data based on the identifiability metric.

9. The device of claim 1, wherein the learning model is updated for each introduction of an additional source of user data.

10. The device of claim 1, wherein the learning model is further based on data received responsive to a challenge request, the challenge request prompted by an inability of satisfying the loss functions.

11. The device of claim 10, wherein the challenge request comprises a request for the user to perform an action, wherein the data that is received responsive to the challenge request corresponds to a physiological response that is perceivable and used to identify the user.

12. A method implemented by one or more computational nodes of a neural network, the method comprising:

generating plural strings of data corresponding to plural sets of user data, the plural sets of user data comprising physiological data, each of the plural strings of data generated based on a learning model, the learning model trained in unsupervised manner using concurrently implemented loss functions that generate each of the plural strings of data in a manner that satisfies the loss functions;

applying a distance metric between the plural strings of data;

providing an indication of authenticity corresponding to a user based on application of the distance metric relative to a threshold; and presenting a challenge request to the user to engage in a monitorable action, the challenge request prompted by an inability of satisfying the loss functions.

13. The method of claim 12, further comprising training the learning model.

14. The method of claim 13, wherein the training further comprises using adversarial conditioning during implementation of the loss functions.

15. The method of claim 12, further comprising determining an identifiability metric based on a loss of the learning model.

16. The method of claim 15, further comprising providing an indication of privacy risk before sharing of the user data based on the identifiability metric.

17. The method of claim 12, further comprising updating the learning model for each introduction of an additional source of user data.

18. A non-transitory, computer readable storage medium that, when executed by one or more processors, causes the one or more processors to:

receive plural strings of data corresponding to plural sets of user data, the plural sets of user data comprising physiological data, each of the plural strings of data generated based on a learning model, the learning model trained in unsupervised manner using concurrently implemented loss functions that generate each of the plural strings of data in a manner that satisfies the loss functions;

apply a distance metric between the plural strings of data;

provide an indication of authenticity corresponding to a user based on application of the distance metric relative to a threshold; and indicate that at least one of the plural strings of data lacks authenticity as being sourced from a source other than the user when the distance metric is higher than a threshold.

19. The non-transitory, computer readable storage medium of claim 18, wherein the learning model comprises a neural network model.

20. The non-transitory, computer readable storage medium of claim 18, wherein the plural sets of user data further comprise data other than physiological data.

* * * * *